United States Patent [19]
Simon et al.

[11] Patent Number: 5,494,640
[45] Date of Patent: Feb. 27, 1996

[54] DEVICE FOR IDENTIFYING AT LEAST ONE GASEOUS COMPONENT IN A GASEOUS OR LIQUID SAMPLE

[75] Inventors: Wilhelm Simon, Hadlaubstrasse 63, 8006 Zurich, Switzerland; Satoshi Ozawa, Hitachi, Japan

[73] Assignees: Hitachi, Ltd., Tokyo, Japan; Wilhelm Simon, Zurich, Switzerland

[21] Appl. No.: 297,009

[22] Filed: Aug. 29, 1994

Related U.S. Application Data

[63] Continuation of Ser. No. 5,201, Jan. 15, 1993, abandoned, which is a continuation of Ser. No. 684,281, Apr. 12, 1991, abandoned.

[30] Foreign Application Priority Data

Apr. 12, 1990 [CH] Switzerland ............... 01285/90

[51] Int. Cl.$^6$ ..................... G01N 33/84; G01N 31/22
[52] U.S. Cl. ............... 422/82.05; 422/68.1; 422/82.08; 422/82.09; 436/68; 436/102; 436/106; 436/109; 436/113; 436/119; 436/164; 436/167; 204/415; 204/418
[58] Field of Search ............ 422/68.1, 82.03–82.08, 422/83, 86, 88, 82.09; 204/415, 416, 418, 419; 435/807, 808; 436/68, 73, 74, 75, 111, 113, 134, 127, 144, 164, 167, 175, 800, 805, 102, 106, 109, 119

[56] References Cited

U.S. PATENT DOCUMENTS

| | | | |
|---|---|---|---|
| 3,754,867 | 8/1973 | Guenther | 23/254 R |
| 4,379,041 | 4/1983 | Petranek et al. | 204/418 |
| 4,529,495 | 7/1985 | Marsoner | 422/82.03 X |
| 4,632,807 | 12/1986 | Marsoner | 422/68 |
| 4,640,820 | 2/1987 | Cooper | 422/68 |
| 4,713,165 | 12/1987 | Conover et al. | 204/403 |
| 4,810,658 | 3/1989 | Shanks et al. | 436/172 |
| 4,824,529 | 4/1989 | Thompson et al. | 204/1 T |
| 4,892,640 | 1/1990 | Wolfbeis et al. | 204/418 |
| 4,973,394 | 11/1990 | Ross et al. | 204/403 |
| 5,057,431 | 10/1991 | Lübbers et al. | 435/208 |
| 5,063,081 | 9/1991 | Cozzette et al. | 422/57 X |
| 5,081,041 | 1/1992 | Yafuso et al. | 436/68 |
| 5,102,526 | 4/1992 | Brown et al. | 204/415 |
| 5,903,490 | 8/1991 | Marsoner et al. | 422/82.01 |

FOREIGN PATENT DOCUMENTS

| | | |
|---|---|---|
| 388248 | 5/1989 | Austria . |
| 0083703 | 7/1983 | European Pat. Off. . |
| 0127106 | 12/1984 | European Pat. Off. . |
| 0344313 | 6/1989 | European Pat. Off. . |
| 0358991 | 3/1990 | European Pat. Off. . |

OTHER PUBLICATIONS

Analyticalsciences, vol. 5, Oct. 1989, pp. 557–561; K. Seiler et al. "Design and characterization of a novel ammonium ion selective optical sensor based on neutral ionophores".

File "Registry" Search Report, Apr. 1995, Copyright ©1995 American Chemical Society (ACS).

*Primary Examiner*—Lyle A. Alexander
*Assistant Examiner*—Long V. Le
*Attorney, Agent, or Firm*—Antonelli, Terry, Stout & Kraus

[57] ABSTRACT

A sensor device is disclosed for identification of a gaseous component in a gaseous or liquid sample. The sensor device comprises an optode membrane having sensitivity for the gaseous component to be identified. The optode membrane incorporates two ionophores, at least one of which is a chromoionophore capable of changing absorption spectrum. The sensor device further comprises a hydrophobic gas-permeable membrane, one side of which is positioned upon the optode membrane to prevent direct contact of the optode membrane with the liquid or gaseous sample while still permitting passage of the gaseous component to be identified. As a result, ionic compounds incapable of passing through the lipophilic gas-permeable membrane do not interfere with the identification process leading to a highly sensitive sensor.

18 Claims, 1 Drawing Sheet

DEVICE FOR IDENTIFYING AT LEAST ONE GASEOUS COMPONENT IN A GASEOUS OR LIQUID SAMPLE

This application is a Continuation application of application Ser. No. 005,201, filed Jan. 15, 1993 (now abandoned), which application is a Continuation application of application Ser. No. 684,281, filed Apr. 12, 1991 (now abandoned).

The present invention relates to a device for identifying at least one gaseous component in a gaseous or liquid sample wherein this device exhibits a solid or semisolid sensor having sensitivity for at least one gaseous component and furthermore comprises a gas-permeable membrane preventing direct contact of the sample with the sensor but being permeable for the passage of at least one gaseous component to be identified.

BACKGROUND OF THE INVENTION

A large number of devices are known for the determination of gaseous components, including those wherein the presence of the gaseous component to be identified can be recognized by optical means.

In a group of the gas sensors known heretofore, the part sensitive with respect to the gaseous component is brought directly into contact with the gaseous sample. Such devices generally exhibit a rather brief response time, but a substantial drawback of these devices resides in that the component responsible for the response effect is, within a rather brief period of time, washed out of the sensor or removed from the surface of the sensor.

Furthermore, sensors are known for the determination of gaseous components in gaseous or liquid samples exhibiting a gas-permeable membrane; when performing the analysis, one side of the gas-permeable membrane is brought into contact with the liquid or gaseous sample, and an electrolyte solution is present on the other side of the gas-permeable membrane, this solution either containing itself an indicator for the penetrating gaseous component or being in contact with a sensor containing the indicator for the gaseous component. Such devices have the disadvantage of a long response time and furthermore are relatively unpleasant to handle, on account of the electrolyte content; they show inadequate stability because of evaporation of the solvent ingredients of the electrolyte solution and they are also sensitive with respect to mechanical damage to the membrane.

It is an object of the present invention to develop a device for the identification of gaseous components in gaseous or liquid samples, this device exhibiting a brief response time combined with a long lifetime, and furthermore being of simple construction, and wherein this device is preferably also suitable for the optical determination of the corresponding gaseous component.

DESCRIPTION OF THE STATE OF THE ART

A large number of devices for the identification of gaseous components in gaseous or liquid samples has been known, exhibiting a sensor which indicates a change as soon as it comes into contact with the component to be identified, for example a sensor which changes its optical properties.

Thus, an optical sensor for fluorescence analysis is described, for example, in U.S. Pat. No. 4,632,807 comprising a measuring chamber through which the liquid or gaseous sample is conducted. The sample comes, during this step, into direct contact with the sensor, the latter containing a fluorescence indicator. The corresponding device is suitable, in particular, for the determination of the partial pressure of oxygen gas or carbon dioxide gas.

The publication by J. F. Giuliani et al. in Optics Letters, vol. 8, No. 1, January 1983, pages 54–56, likewise describes an optical sensor wherein a layer of the organochemical sensor, being an oxazine perchlorate dye, is present as a coating on a glass substrate, for example on the outside of a corresponding glass capillary which latter had been rough-etched with hydrogen fluoride prior to application of the indicator dye in order to ensure an improved anchorage of the indicator on the glass carrier. Also in this case, a direct contact of the indicator layer sensitive to gaseous ammonia is effected with the gaseous sample.

One disadvantage of these devices resides in that the indicator is relatively easily removable from the surface on which it is provided, even if the surface has been roughened by a preliminary etching step.

An attempt has been made to avoid these drawbacks by incorporating the indicator into synthetic resin materials. Thus, the publication by K. Seiler, W. E. Morf, B. Rusterholz and W. Simon, in Analytical Sciences, vol. 5, October 1989, pages 557–561, e.g., describes an optical sensor for the analysis of ammonium ions in liquid samples wherein a sensor membrane provided on an inert support material is brought directly into contact with the liquid sample. The sensor membrane consists of a synthetic resin wherein an ionophore selective for ammonium ions, as well as a chromoionophore selective for protons are embedded. Upon bringing this sensor membrane into contact with the component to be identified, namely ammonium ions, then complex formation occurs between the ionophore contained in the sensor membrane and sensitive to ammonium ions, and during this complexing reaction, protons are furthermore released so that thereby the chromoionophore, selective for protons, changes its color. The concentration of the ammonium ions in the sample is determined based on the extent of this optical change. A mixture of nonactin and monactin is utilized as the lipophilic complexing agent selective for ammonium ions, i.e. as the ionophore. This device, in comparison with devices utilized previously, is very advantageous because the pH-sensitive chromoionophore will respond only if the component to be identified, namely the ammonium ions, indeed penetrate from the sample solution into the corresponding synthetic resin membrane. Also the problems of washing out of indicator materials by the sample solution are substantially reduced with respect to previously known systems, on account of the embedding of the indicator combination of ammonium-selective ionophore and proton-selective chromoionophore. A substantial drawback of this device resides in that the complexing agent selective with respect to ammonium ions and lacking a chromophore group will also form complexes with other ions, e.g. potassium ions. The analysis is falsified in case the sample solution contains such interfering ions.

In the publication by Q. Zhou et al. in Applied Optics, vol. 28, No. 11, June 1989, pages 2022–2025, likewise stemming from the most recent time, a sensor is disclosed for the determination of ammonia, containing porous synthetic resin fibers as the optical sensor. These porous synthetic resin fibers exhibit a uniform pore size and, as can be seen from FIG. 1 on page 2023 of this publication, the porous fiber section containing the indicator is, in this analysis, brought directly into contact with the liquid or gaseous sample, and the ends of this porous section are retained by means of a "Teflon" capillary. Response thus takes place exclusively at the exposed part of the fiber section, i.e. not in that portion which is enclosed within the supporting "Teflon" capillary. The synthetic resin component of these porous fibers is a copolymer of methyl methacrylate and triethylene glycol dimethacrylate wherein this copolymer has been rendered porous by chemical agents. The indicator for ammonia utilized therein is an indicator for ammonia that has been known for a long time, namely bromcresol purple.

Porous optical fibers based on a borosilicate glass, containing an indicator for ammonia in the porous surface, have furthermore been described in the publication by Shahriari et al. in Optics Letters, vol. 13, No. 5, May 1988, pages 407–409. Here again, there is direct contact between the liquid or gaseous sample and the optical sensor, and this reference also employs, as the colorimetric indicator for the ammonia, the indicator bromcresol purple, known for a long time.

The publication by O. S. Wolfbeis and H. E. Posch in Analytica Chimica Acta, vol. 185, July 1986, pages 321–327, also discloses an optical sensor for ammonia, based on a fiber-optic system and a fluorescence indicator. In this case, too, the sensor is brought into direct contact with the liquid or gaseous sample, and the problems of washing out of the indicator are avoided by emulsifying the aqueous indicator solution in a liquid silicone prepolymer, and then further polymerizing the prepolymer into a silicone rubber, thereby enclosing the emulsified droplets of the indicator solution within the rubber. This sensor with emulsified liquid indicator exhibits the disadvantage of a relatively long response time of 2–5 minutes and of a response time which is dependent on the size of the emulsified aqueous droplets. Besides, acids, respectively acidic gases, impair the analysis.

Furthermore, gas-permeable membranes, for example of "Teflon", have been known which exhibit permeability for carbon dioxide, oxygen, and ammonia. The publication by D. W. Lübbers and N. Opitz, in "Zeitschrift fuer Naturforschung" [Natural Sciences Journal], vol. 30 c, 1975, pages 532, 533, already describes a device for the optical identification of carbon dioxide or, respectively, oxygen, in liquid or gaseous samples wherein an indicator chamber containing an aqueous solution of a fluorescence indicator is separated from the gaseous or liquid sample by a gas-permeable "Teflon" membrane having generally a thickness of 6 μm to 12 μm. The corresponding device has a rather low sensitivity because the volume of indicator solution present behind the permeable membrane is relatively large, and thus a response of the optical indicator solution can be observed only after passage of relatively large amounts of the gaseous component to be identified through the gas-permeable membrane. Besides, the thin, freely stretched membrane separating the sample chamber from the indicator chamber is obviously very sensitive to mechanical damage.

An optical sensor for the identification of ammonia has been described in the publication by M. A. Arnold and T. J. Ostler in Analytical Chemistry, vol. 58, May 1986, pages 1137–1140; this sensor has an internal electrolyte solution which contains a pH indicator dye. The lightguide is dipped into this electrolyte solution, and the electrolyte solution is separated from the sample by means of a gas-permeable membrane of "Teflon". On account of the fact that the volume of the aqueous electrolyte solution is kept very small, it is possible to detect ammonia down to a lower limit of 5 μmolar.

The gas-permeable membrane, however, also shows permeability for the water molecules of the electrolyte solution. For this reason, the corresponding sensor will become useless already after a short usage period due to drying out of the electrolyte. A further drawback of these sensors resides in that any materials having acidic or alkaline properties, passing through the gas-permeable membrane, will falsify the measured value by altering the pH value of the electrolyte solution containing the pH indicator.

In most recent times, F. L. Dickert et al. have described, in Analytical Chemistry, vol. 61, October 1989, pages 2306–2309, a device for the optical identification of organic solvents in wastewaters. This device contains, as the indicator, a substituted 3,3-diphenyl phthalide which yields, by interaction with an acidic component, for example a phenol, strongly colored triphenylmethane dyes. A layer of this sensor is disposed on the surface of a lightguide, and the sensor layer is separated from the gas-permeable membrane, which latter prevents direct contact of the sensor with the water sample, by means of an air gap. This device thus contains no electrolyte solution between the gas-permeable membrane and the sensor layer, and consequently the problems connected with drying out of the electrolyte solution are avoided. Furthermore, as can be seen from FIG. 1 on page 2307 of this publication, the gas volume between the sensor and the gas-permeable membrane is kept at a small value in order to shorten the response time of the sensor. A direct contact of the indicator layer with the gas-permeable membrane, however, has been carefully avoided since it was apparently assumed that, upon direct contact, a migration of the indicator molecules into the gas-permeable membrane would take place and thus the gas permeability of the membrane would be impaired. In order to mechanically protect the thin, gas-permeable membrane and yet ensure access of the gaseous components of the aqueous samples to the gas-permeable membrane, a perforated metallic lid was utilized.

In European Patent Publication No. 0 358 991, published on Mar. 21, 1990, a testing device for the optical determination of cations in aqueous sample solutions has furthermore been disclosed, containing in a carrier material a cation-selective lipophilic ionophore in combination with an anion-selective lipophilic ionophore or a cation exchanger. As a result, upon performance of the analysis, a coextraction of the cation with an anion from the sample solution into the sensor takes place, or an exchange of a cation of the sensor against the cation to be analyzed, stemming from the sample solution, is effected. One of the aforementioned components must furthermore exhibit a chromophoric group which changes its optical properties as soon as it comes into contact with the cation to be determined or with a secondary product released upon binding of the cation to be determined to the ionophore. Analogous designs, with anion-selective ionophore, have been described for the identification of anions in aqueous sample solutions. These disclosures also include lipophilic chromoionophores selective with respect to protons. Although corresponding cation-selective lipophilic ionophores frequently exhibit good selectivity for the cation to be identified in the sample solution, as compared with other, additional cations that may be present in the sample solution, other cations contained in the sample solutions frequently cause trouble, after all, during the practical conductance of measurements of a specific cation. Analogous conditions prevail in the identification of anions with anion-selective ionophores.

DESCRIPTION OF THE INVENTION

As can be seen from the preceding paragraphs, devices for the identification of at least one gaseous component in a gaseous or liquid sample have been known wherein the corresponding devices exhibit a sensor having a sensitivity for the component to be identified and wherein furthermore several of the known devices additionally contain a gas-permeable membrane with permeability for the gaseous component, to be analyzed, of the gaseous or liquid sample wherein, however, direct contact of the sensor with this sample is prevented.

It has been assumed heretofore that it is absolutely necessary to provide, between the side of the membrane facing the sensor and the sensor, an electrolyte solution or a gas volume, preventing direct contact between the gas-permeable membrane and the sensor by means of this liquid or gaseous medium. For it has been assumed heretofore that components present in the sensor would destroy the gas selective permeability of the gas-permeable membrane within a short period of time, in case of direct contact with this membrane; alternatively, it has been assumed heretofore that the presence of an electrolyte is absolutely required to permit identification of the component to be analyzed which passes through the gaseous membrane.

It has now been found, surprisingly, that none of the expected drawbacks occur upon direct contact of the gas-permeable membrane with the sensor, and that furthermore corresponding devices possess a far higher sensitivity and a substantially shorter response time, in comparison with devices wherein an electrolyte or a gaseous space is provided between the gas-permeable membrane and the sensor.

Therefore, one object of the present invention is a device for the identification of at least one gaseous component in a gaseous or liquid sample, wherein this device (A) exhibits a solid or semisolid sensor having sensitivity for the at least one component to be identified, and (B) comprises a gas-permeable membrane, one side of which, during performance of the analysis, is in contact with the gaseous or liquid sample, and which prevents direct contact of the sensor A with the sample, and wherein the gas-permeable membrane shows permeability for the at least one component of the sample to be determined, wherein this device is characterized in that the gas-permeable membrane B is located directly on the solid or semisolid sensor A and is mechanically supported by this sensor.

On account of the feature that the gas-permeable membrane is mechanically supported by the solid or semisolid sensor, a very simple structure of the device becomes possible without having to use any protective elements equipped with penetration possibilities for the sample, such as perforated metal lids, in order to protect the membrane. By virtue of the fact that no protective elements are provided between the membrane surface, coming into contact with the liquid or gaseous sample, and the corresponding sample, no effective surfaces of the gas-permeable membrane are covered up, either, and thus passage of the gaseous component to be analyzed through the gas-permeable membrane can take place immediately upon contact of the gas-permeable membrane with the gaseous or liquid sample. This alone ensures a substantially shorter response time, as compared with heretofore conventional, corresponding devices. Besides, on account of the fact that the sensor A mechanically supports the gas-permeable membrane in contact therewith, the corresponding membrane can be made even thinner than has been the case with gas-permeable membranes utilized thus far. The thinner the gas-permeable membrane, the faster can be gaseous component of the sample pass therethrough, and the more quickly is the final measured value attained, i.e. the shorter is the response time.

As mentioned above, the devices known heretofore provided for a gaseous volume or an electrolyte volume between the gas-permeable membrane and the sensor. The measured value was achieved only after an equilibrium concentration had been established between the gaseous component to be determined in the gaseous or liquid sample and the gaseous components to be determined in the gas- or electrolyte-filled interspace between the gas-permeable membrane and the sensor. The larger this space filled with a gas or electrolyte, the longer is the time required for attaining the equilibrium condition and, furthermore, larger volumes of this interspace lower the sensitivity of the device. In cases with an especially disadvantageous circumstance, a falsification of the measured value could even occur by a lowering of the concentration of the component to be identified in the gaseous or liquid sample, due to the transgression of this component from the sample via the gas-permeable membrane into the gas-filled or liquid-filled space between the membrane and the sensor.

All of these aforementioned disadvantages are avoided with the device according to this invention by direct contact of the gas-permeable membrane with the sensor.

According to a preferred embodiment of the present invention, the device is fashioned so that it is suitable for the identification of gaseous components in the sample wherein the corresponding gaseous components form at least one ionic species after passage through the gas-permeable membrane in and/or on the sensor, or with a further component that may be present in and/or on the sensor. Examples of components promoting formation of ionic components from the gaseous component that has passed through the gas-permeable membrane are any materials that bind the corresponding ionic component, such as, for example, those forming a salt or a complex therewith.

Examples that can be cited for gaseous components capable, after passing through the gas-permeable membrane, of forming at least one ionic species are carbon dioxide, nitrous gases, sulfur dioxide, phosgene, hydrogen sulfide, thiols, hydrogen halides, hydrogen cyanide, low-molecular organic acids, ammonia, and low-molecular amines.

Devices comprising an ion-selective part which contains a lipophilic ion-selective component, namely a so-called ion carrier, have been utilized for a long time for the electrometric determination of the corresponding ions for which the carrier in question has selectivity, in liquid samples. Corresponding lipophilic carriers for the at least one ionic component formed from the gaseous component are utilized with advantage in and/or on the sensors of the devices according to this invention.

In accordance with a preferred embodiment of the invention, the device is one which permits the optical identification of at least one gaseous component in the gaseous or liquid sample. These preferred devices comprise, as the sensor A, an optical sensor changing at least one of its optical properties in the ultraviolet light range, in the visible light range, or in the infrared light range, as soon as it comes into contact with at least one component of the sample to be identified. In appropriate optical sensors, the change in optical properties generally is constituted by extinction of fluorescence, production of fluorescence, or alteration of light absorption in a specific wavelength range. If the change in light absorption takes place in the visible wavelength range, then this change can bring about an alteration in color, produce a color, or make a color disappear.

In and/or on the optical sensor, at least one component can be present which varies its optical properties as soon as it comes into contact with the gaseous component to be determined; or at least one first component can be present in the sensor and/or on the sensor which enters into interaction with the gaseous component to be identified and thereby, for example by the release of a secondary product, evokes a change of an optical property in a second component contained in the sensor or on the sensor.

As has been mentioned above, preferred gaseous components to be identified by means of the device according to this invention are those which, after passing through the gas-permeable membrane onto or, respectively, into the sensor, are capable of forming at least one ionic species; and preferably the sensor furthermore contains a lipophilic ion-selective component exhibiting selectivity for the ionic species formed from the gaseous species. In case of the optical sensors, these contain, according to a preferred embodiment of the invention, a lipophilic complexing agent having selectivity for the ion formed from the gaseous component wherein the form of the complexing agent, complexed with the ionic component, differs in at least one of its optical properties from the corresponding uncomplexed form of the complexing agent.

Keto compounds forming complexes or, respectively, adducts with the anions of oxa acids, for example with carbonate anions, bicarbonate anions, sulfite anions, the anions of nitric acid or nitrous acid, or the anions of organic acids, are described in European Patent Publication No. 0 281 829. In this reference, also those keto compounds are recited which exhibit a chromophoric group where, in this case, the free keto compound differs in its optical properties from the adduct of the keto compound with the anion of the oxa acid. These keto compounds described therein which exhibit a chromophoric group can be utilized as a component in the optical sensors of the device according to this invention in case the gaseous component to be identified is suited for the formation of an anion of an oxa acid or can evoke the formation of a corresponding anion of an oxa acid in a further component that is present.

According to another embodiment of the corresponding optical sensors of the devices of this invention, this sensor contains, in addition to the complex-forming agent which forms a complex with the ionic species produced from the gaseous component, still another component which enters into interaction with a product released during complex formation, or with an educt, thereby altering an optical property of this second component, for example a change in the optical properties of a pH indicator based on a release of protons, or a consumption of protons during the complexing reaction between the ionic species and the complexing agent for the same.

In case a proton is liberated or consumed during the complex formation between the ionophore and the ionic species formed from the gaseous species, then a conventional pH indicator can be utilized as the component for changing the optical properties, but it is even more advantageous to use a lipophilic ionophore that has been most recently developed and is selective with respect to protons, this ionophore differing in the protonated form from the unprotonated form with respect to light absorption, for example changing its color. Such proton-selective lipophilic ionophores and testing units containing same are described in European Patent Publication No. 0 358 991 published on Mar. 21, 1990. Still more novel compounds have now been developed which form lipophilic complexes with protons and wherein the protonated form differs spectroscopically from the unprotonated form.

Several reaction pathways have been determined for the reactions with the lipophilic chromoionophore taking place in the sensor.

The neutral form of the proton-selective chromoionophore of formula C can be converted, by protonating, into the corresponding acidic form of the formula $CH^+$.

Furthermore, the neutral form of the proton-selective chromoionophore of the formula CH can be converted by deprotonating into the corresponding basic form $C^-$.

In both instances, it is merely important that the unprotonated form differ from the protonated form with respect to an optical property.

If L represents the ionophore that does not exhibit a chromophoric group, which forms a complex with the gaseous component to be analyzed, stemming from the sample, protons being taken up and, respectively, released during this reaction, then the corresponding reaction with the proton-selective chromoionophore can be illustrated by the following reaction schemes 1 and 2: In this reaction scheme, G represents a gaseous species having basic properties, which species is to be identified and which is capable, on account of its basic properties, of forming an ion of the formula $GH^+$. As one example thereof, the reaction $$NH_3 + H^+ \rightleftharpoons NH_4^+$$

can be cited.

In the reaction scheme below, GH furthermore means a gaseous species exhibiting acidic properties capable, on account of its acidic properties, of forming ions of the formula $G^-$. As an example thereof, the reaction scheme $$HCN \rightleftharpoons H^+ + CN^-$$

can be cited.

In the reaction scheme below, the index s furthermore means the species of the gaseous component present in the sample while the corresponding species shown without the index s illustrates the form present in the sensor:

$$L + CH + G(s) \rightleftharpoons L\text{-}GH^+ + C^- \tag{1}$$

$$L + C + GH(s) \rightleftharpoons L\text{-}G^- + CH^+ \tag{2}$$

In some cases, however, additional ions $R^+$ and $R^-$ may be required in order to maintain the electroneutrality of the optode membrane. In this case, the reaction takes place, instead of proceeding in accordance with the above-mentioned schemes 1 and 2, according to the following schemes 3 and 4:

$$L + CH^+ + R^- + G(s) \rightleftharpoons L\text{-}GH^+ + C + R^- \tag{3}$$

$$L + C^- + R^+ + GH(s) \rightleftharpoons L\text{-}G^- + CH + R^+ \tag{4}$$

There are also instances wherein the gaseous species passing through the gas-permeable membrane is capable of formation of an ionic species only in the presence of water. One example in this connection is the reaction scheme $$CO_2 + H_2O \rightleftharpoons H^+ + HCO_3^-$$

The gas-permeable membrane utilized in the devices according to this invention is also permeable for water vapor. Accordingly, the small amounts of water that may be required for the formation of an ionic species from the gaseous species passing through the gas-permeable membrane, for example in the determination of carbon dioxide according to the above reaction scheme, are always present because water molecules stemming from the sample solution or from the atmospheric humidity are present on the surface of the sensor or in the sensor proper.

The sensor, exhibiting sensitivity for at least one component to be identified, generally contains a component showing the appropriate sensitivity embedded in an inert material, for example a corresponding lipophilic ionophore and/or a lipophilic chromoionophore, incorporated into a synthetic resin matrix.

Preferred examples of a corresponding polymer material for the sensor are polyester polymers and polymeric materials stemming from olefinic monomer units wherein, in both cases, homopolymers as well as copolymers are suitable. Specifically preferred for use are those polymer materials utilized already for a long time as the polymer component of ion-selective membranes for the electrometric determination of ion concentrations; these conventional ion-selective membranes contain, as the ion-selective component, a complex-forming compound for the type of ion to be identified, i.e. an ionophore, for example a dicarboxylic acid diamide exhibiting lipophilic properties. The polymer component of such ion-selective membranes for the electrolytical determination of ion concentration in sample solutions is generally a homopolymer or copolymer of vinyl halogenides, particularly a homopolymer or copolymer of vinyl chloride or vinylidene chloride, and specifically preferably a vinyl chloride homopolymer or a copolymer of vinyl chloride with substantially lesser proportions of vinyl alcohol.

It is readily apparent that, if in the device according to this invention the sensor A responsive to the component that has passed through the gas-permeable membrane exhibits a relatively small volume, then minimum quantities of the gaseous component to be identified will trigger a response of the sensor. Accordingly, in a preferred embodiment of the invention, the solid or semisolid sensor A is designed in the form of a membrane disposed on a solid, light-permeable carrier material.

In such membrane-shaped sensors, the polymer material is frequently one which contains a plasticizer as an additional component, particularly a plasticizer having lipophilic properties. Examples of corresponding plasticizers that can be cited are, again, those which are generally employed in ion-sensitive membranes for the electrometric determination of ion concentrations in liquid sample solutions, such as, for example, esters of dicarboxylic acids, such as sebacic acid or adipic acid, with longer-chain aliphatic alcohols, e.g. alcohols of at least 5, preferably at least 7 carbon atoms, as well as esters of tetracarboxylic acids with higher aliphatic alcohols, for example the corresponding esters of benzophenonetetracarboxylic acid or benzhydroltetracarboxylic acid. Furthermore suitable are esters of phosphoric acid with longer aliphatic alcohols or ethers exhibiting at least one longer aliphatic residue, such as, for example, the o-nitrophenyloctyl ether.

In case the sensor of the device according to this invention operates according to the reaction schemes 3 and 4, an additional ionic species $R^-$ or $R^+$ is necessary to maintain the electroneutrality of the membrane-shaped sensor. Based on the lipophilic properties of the polymer matrix, additional ionic species $R^-$ or $R^+$ is to exhibit lipophilic properties as well. Accordingly, preferred ionic species $R^-$ are introduced into the membrane as salts with an exchangeable cation, e.g. corresponding alkali metal salts. An example for a suitable lipophilic anion $R^-$ that can be cited is a borate that exhibits at least one lipophilic residue. However, borates with more than one lipophilic residue are preferred, especially tetraalkyl or tetraaryl borates. Specific examples that can be cited are the corresponding tetraphenylborates which optionally carry substituents additionally in the benzene nucleus, such as, for example, chlorine atoms.

Examples of ionic species $R^+$ exhibiting lipophilic properties, for anionic species, are corresponding quaternary ammonium ions, and are introduced into the membrane as salts of relatively small anions, such as, for example, halogenides. The corresponding ammonium salts must exhibit, for attaining the required lipophilic properties, at least one lipophilic organic residue, and methyltridodecylammonium chloride can be cited as a corresponding example.

In the devices according to this invention, a thin membrane of a hydrophobic material is utilized as the gas-permeable membrane B, having the corresponding gas permeability. Such gas-permeable membranes have been known from the technical literature. Examples for well-suitable polymer materials of the gas-permeable membrane B are olefin polymers of optionally halogen substituted olefins. Accordingly, the gas-permeable membranes preferably contain polyethylene, polypropylene, or polymers of fluorinated or chlorinated alkenes, e.g. polytetrafluoroethylene, or they consist of such olefin polymers. The material of the gas-permeable hydrophobic membrane can, however, also be a silicone, and silicone rubber can be cited as an example in this connection.

It is known that the gas-permeable membranes which function according to their hydrophobic properties lose their gas selective permeability if they are impregnated by lipophilic components, especially corresponding higher-molecular organic compounds. This also appears to be a reason why heretofore no attempts have been made by experts in this field of bringing a gas-permeable membrane into direct contact with a sensor carrying a polymer matrix, because experts have assumed that lipophilic components contained in the sensor, such as, for example, ion carriers having lipophilic properties, plasticizers that may be present and exhibit lipophilic properties, and similar ingredients, would impregnate through the gas-permeable membrane and thus render the gas selective permeability ineffective within a minimum of time, in case of direct contact of the gas-permeable membrane with the sensor.

It has been found surprisingly that these expected problems did not materialize and that therefore unexpected advantages can be achieved by means of the direct contact, established in the devices of this invention, of the gas-permeable membrane B with the solid or semisolid sensor, for example a corresponding membrane-shaped sensor exhibiting a synthetic resin matrix.

As has been explained in detail above, the solid or semisold sensor contains, according to a preferred embodiment of the invention, a so-called ion carrier, i.e. a complexing agent forming selectively a complex with an ionic species formed from a gaseous species. Corresponding sensors for the identification of ionic species, which are dipped directly into a corresponding liquid sample solution, without the use of a gas-permeable membrane, are in use in many areas of analytical technique, including those ion-selective sensors wherein the presence of the ion to be determined is confirmed by an optical method in a qualitative or quantitative fashion.

It is known that the complexing agents for the ion to be identified, contained in the sensors as the ion-selective component, do exhibit a selectivity for the ion to be determined, in comparison with other ions that may be present in the sample solution, but that great difficulties arise if relatively large amounts of interfering foreign ions are contained in the sample solution. Ion-selective components for ammonium ions generally also exhibit complexing properties for potassium ions and it is correspondingly impossible to determine, with such ion-selective devices, the concentration of ammonium ions in sample solutions by the optical or electrometric method, if potassium ions are likewise contained in the sample solution.

These known drawbacks are eliminated by the device according to this invention. On account of the fact that a direct contact of the solid or semisolid sensor A with a liquid sample is prevented by the gas-permeable membrane B, only those species which can pass through the gas-permeable membrane can reach the sensor. Any ionogenic species which are incapable of passing through the gas-permeable membrane are accordingly kept away from the sensor and thus cannot interfere with the identification process.

Accordingly, it is possible by means of the device according to this invention, for example, to determine ammonia in aqueous samples if large amounts of cations are present in these samples which would interfere with the response of the sensor, such as, for example, potassium ions. The ammonia passes through the gas-permeable membrane, but the inorganic cations, such as potassium, are kept away from the sensor A by the gas-permeable membrane B.

The circumstances are analogous in case the component to be identified, passing through the gas-permeable membrane, is capable of forming anions, such as, for example, carbonate anions and sulfite anions. Also in this case, such anionic components present in the aqueous sample solution which cannot pass through the gas-permeable membrane do not interfere, such as, for example, sulfate anions phosphate anions, or borate anions.

A further subject of the present invention resides in a process for the identification of at least one gaseous component in a gaseous or liquid sample with the use of a device according to this invention, wherein this process is characterized in that the gas-permeable membrane B of the device is brought into contact with the liquid or gaseous sample, the component to be identified passing through the gas-permeable membrane and reaching the surface of the solid or semisolid sensor A, which latter is in direct contact with this gas-permeable membrane B, and the component to be identified causes on the sensor and/or in the sensor, on account of the sensitivity of the latter with respect to the component to be identified, a detectable change, for example an optically detectable change, and wherein any further components that may be present in the sample and which cannot penetrate the gas-permeable membrane B are kept away from the sensor A, thus preventing an impairment of the identification by such possibly present further components.

The invention will now be described in greater detail with the aid of examples which nowise are to limit the idea of this invention.

BRIEF DESCRIPTION OF THE DRAWING

Example 1

A preferred embodiment of a device according to this invention will be demonstrated with reference to this example and to FIG. 1.

Figure 1:
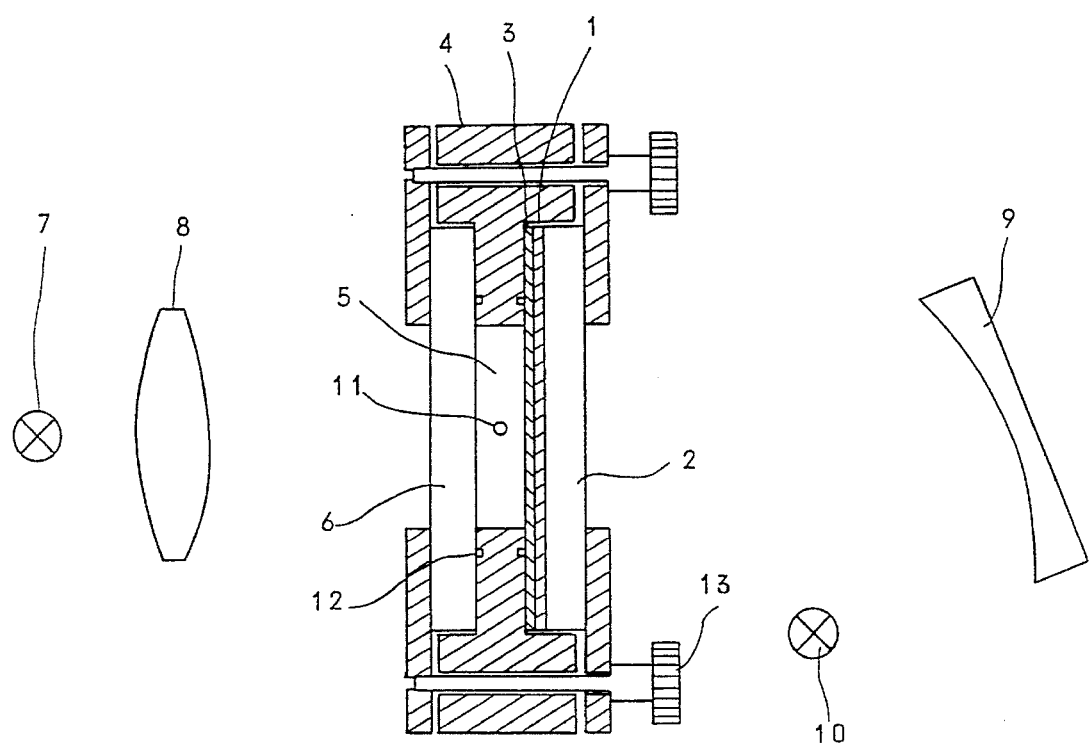

This device (4) is provided with a chamber (5) into which the gaseous or liquid sample to be identified is introduced via the opening (11). This chamber (5) is defined by plates of a light-transmitting material, for example quartz (6) and, respectively, (2). The optical sensor (1) fashioned in the shape of a membrane is arranged on the light-permeable plate (2) and the gas-permeable membrane (3) is located there above. The chamber (5) is sealed by means of the sealing elements illustrated in shaded form, with the use of O rings (12), the fixation of the sealing elements being ensured with the aid of the screws (13).

The device is illuminated by means of a light source (7), for example a halogen lamp, and the light from this light source enters, via the condenser (8) and the light-permeable plate (6), into the cell (5) which contains the sample, and from there impinges upon the gas-permeable membrane (3), the optode membrane (1), and exits again through the light-permeable plate (2). The light that has passed through the device then impinges upon a concave optical grating (9) and from there is transmitted to the detector (10) and examined for its optical properties.

It can be seen that in the device the liquid or gaseous sample present in the chamber (5) is in contact with the gas-permeable membrane (3) and consequently a large area is available through which the gaseous component to be identified can pass and can come into contact with the optode membrane (1). In the corresponding optode membrane, the gaseous component to be identified then evokes an optical change which is proportional to the content of gaseous component to be identified in the sample. Accordingly, the device of FIG. 1 can be used for performing a quantitative determination of the gaseous component. The gas-permeable membrane which is microporous, for example an appropriate membrane of polytetrafluoroethylene, has, in the embodiment illustrated herein, a thickness of 5–9 μm, for example a thickness of 7 μm. On account of the fact that this gas-permeable membrane is mechanically supported by the optode membrane (1) in contact therewith, and that membrane, in turn, rests on the light-transmissive plate (2) and is carried thereby, the gas-permeable membrane is not under any mechanical stress and consequently also the aforementioned, very thin gas-permeable membranes are well protected against mechanical destruction.

Example 2

The production of an optode membrane for the optical identification of ammonia will be described with the aid of this example.

Two versions of this membrane were produced; one of the two versions contained 2.4% by weight of nonactin as the ion-selective component for the ammonium ions, and the other one of the two membranes contained an equimolar amount of valinomycin. Furthermore, the membrane contained 1.6% by weight of a chromoionophore sensitive with respect to protons, as well as 1.5% by weight of the cation exchanger potassium tetrakis(p-chlorophenylborate).

Furthermore, the membrane contained 63.0% by weight of a plasticizer based on a sebacic acid ester, namely bis(2-ethylhexyl)sebacate, and 31.5% by weight of polymer material, namely poly(vinyl chloride) as the carrier.

The purity of the nonactin employed was about 75% by weight, the remaining 25% by weight consisted of the homologous monactin which, however, had no effect on the determination of the ammonium ions.

As the proton-selective chromoionophore, a compound was chosen covered by the general Formula II

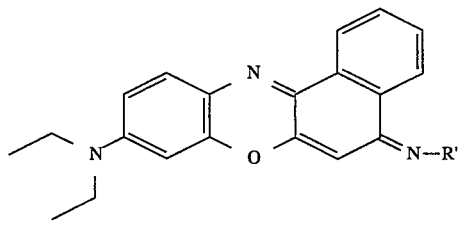

of the chromoionophores disclosed in European Patent Publication 0 358 991 where, in this formula, the residue R' is an aliphatic residue directly linked to the nitrogen atom and containing at least 10 carbon atoms.

In the present case, this residue R' was an n-decyl residue substituted in the 2-position with respect to the linkage site to the nitrogen atom by an n-octyl residue. This residue R' thus exhibited the following structure

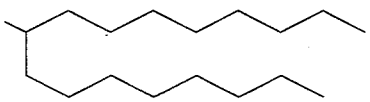

This specific proton-selective chromoionophore is not mentioned in so many words in the aforementioned European patent publication.

In order to produce the membrane, the above-mentioned components were mixed in the indicated quantitative ratios so that a total weight of 120 mg was the result. These 120 mg were dissolved in 0.75 ml of tetrahydrofuran and applied to a quartz plate so that, after evaporation of the solvent, a uniform layer of the optode membrane was obtained with a thickness of about 3 μm.

By conditioning the optode membrane provided on the quartz plate with an aqueous phosphate buffer solution of a pH of 7.0, the objective was achieved that the proton-selective chromoionophore of the above-indicated structure was converted into the protonated form, namely in that protons entered the membrane, and the potassium ions of the ion exchanger exited from the membrane, supposedly in quantitative fashion.

The valinomycin, utilized as a sensor for the ammonium ions according to the one version, has, as is known, a substantially higher selectivity for potassium ions than for ammonium ions. However, since in the present case, after conditioning, the gas-permeable membrane of tetrafluoroethylene was applied to the optode membrane, the corresponding device could be utilized for the identification of ammonia in gaseous and, respectively, liquid samples. The corresponding optode membrane, containing valinomycin, thus is not impaired by potassium ions that may be present in an aqueous sample solution because, when using this membrane in the device illustrated in FIG. 1, the gas-permeable membrane (3) prevents access of the potassium ions to the optode membrane.

Example 3

The production of an optode membrane for the determination of carbon dioxide will be described with reference to this example.

The optode membrane was produced in accordance with the method disclosed in Example 2 but using, in the present case, 6.3% by weight of methyltridodecylammonium chloride as the so-called ion-selective component for the bicarbonate anions formed from carbon dioxide.

The corresponding membrane contained furthermore a novel pH indicator modified by introduction of a lipophilic group, namely a corresponding derivative of umbelliferone, i.e. of 7-hydroxycoumarin.

This novel pH indicator exhibiting lipophilic properties corresponds to the following Formula III

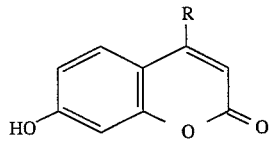

wherein R means a substituent having lipophilic properties, especially a directly bound alkyl residue of at least 10 carbon atoms, an aryl residue, an aryl residue substituted by an alkyl residue of at least 10 carbon atoms, or optionally the residue R of the above-indicated type also may be bound to the carbon atom of the heterocycle, rather than directly, by way of a divalent grouping, for example an ether group or an ester grouping.

In the present example, the pH indicator employed was a compound of Formula III wherein the residue R is a straight-chain alkyl residue of 17 carbon atoms, i.e. 4-heptadecyl-7-hydroxycoumarin.

In the manufacture of the optode membrane, this proton-selective chromoionophore was utilized in a quantity of 4.3% by weight, and furthermore 58.1% by weight of the plasticizer bis(2-ethylhexyl) sebacate and 31.3% by weight of polyvinyl chloride were utilized. The corresponding optode membrane, selective with respect to bicarbonate anions, was cast in the manner described in Example 2 with the use of a solvent and, after conditioning of this membrane, the gas-permeable membrane of tetrafluoroethylene was applied to this membrane.

When identifying carbon dioxide in the gaseous or liquid sample, the carbon dioxide passes through the gas-permeable membrane and subsequently forms the bicarbonate anion with the water molecules present in the optode membrane. This anion enters into interaction with the ionophore, namely the lipophilic methyltridodecylammonium cation, and the chromoionophore for the protons, namely 4-heptadecyl-7-hydroxycoumarin, responds to the protons released during this total reaction. The course of the reactions can be illustrated by the following reaction scheme:

$$L^+ + C^- + CO_2(s) + H_2O \rightleftharpoons L^+ - HCO_3^- + CH$$

In this reaction scheme, $L^+$ means methyltridodecylammonium ion, i.e. the so-called ionophore, $C^-$ is the chromoionophore for the protons in its deprotonated condition (splitting off of the proton of the phenolic hydroxy group of 7-hydroxycoumarin), while CH means the corresponding protonated product.

The corresponding identification of carbon dioxide was performed in a nitrogen gas at 100% humidity.

It was found that the corresponding sensor is specifically advantageous for carbon dioxide in order to identify carbon dioxide in physiological samples.

We claim:

1. A device for identification of a gaseous component in a liquid sample, comprising:

1) a sensor comprising a lipophilic polymer material, at least one ionophore, and ion forming material for forming at least one ionic species from the gaseous component or from the gaseous component and a further component that is present in and/or on the sensor, said at least one ionophore having a sensitivity for the at least one ionic species, and 2) a hydrophobic gas-permeable membrane for preventing permeation of ions dissolved in the liquid sample, but permitting permeation of said gaseous component, one side of which is in contact with the liquid sample, said hydrophobic gas-permeable membrane being positioned upon said sensor to prevent direct contact between said sensor and said liquid sample and wherein said hydrophobic gas-permeable membrane is supported by said sensor, wherein said identification of said gaseous component is performed by quantitating changes induced by reaction of said ion forming material with said gaseous component, or a reaction product of said gaseous component and said further component, said reaction generating said at least one ionic species.

2. A device according to claim 1, wherein said device further comprises an optical detector, said ion forming material comprising a chromoionophore capable of changing optical properties thereof upon reaction of the gaseous component with the sensor.

3. A device according to claim 2, said device further comprising a light source for transmitting light towards said detector via a chamber containing said sample, said hydrophobic gas-permeable membrane.

4. A device according to claim 1, wherein said gaseous component has an ability to pass through the hydrophobic gas-permeable membrane and to form the at least one ionic species, and wherein said gaseous component is selected from the group consisting of carbon dioxide, nitrous gases, sulfur dioxides phosgene, hydrogen sulfide, thiols, hydrogen halides, hydrogen cyanide, lower organic acids, ammonia and amines.

5. A device according to claim 1, wherein said lipophilic polymer material is a polymer matrix.

6. A device according to claim 1, wherein said lipophilic polymer material contains a plasticizer.

7. A device according to claim 1, wherein said sensor further comprises an ionic compound to maintain electroneutrality of the sensor within said polymer material.

8. A device according to claim 1, wherein said ionophore is a lipophilic compound capable of complexing with an ion formed from the gaseous component to be identified.

9. A device according to claim 1, wherein said hydrophobic gas-permeable membrane is a polymer.

10. A device according to claim 9, wherein said polymer is an olefin polymer.

11. A device according to claim 10, wherein said olefin polymer is a halogen substituted olefin polymer.

12. A device according to claim 2, wherein said chromoionophore varies optical properties thereof in the ultraviolet light range, in the visible light range or in the infrared light range.

13. A device according to claim 12, wherein said chromoionophore varies the optical properties upon complexation with ions generated by reaction of said at least one ionic species with said ionophore.

14. A device according to claim 13, wherein said chromoionophore varies the optical properties upon complexation with hydrogen ions generated by reaction of said at least one ionic species with said ionophore.

15. A device according to claim 1, wherein said gaseous component to be identified forms an ionic compound upon contact with said sensor.

16. A device according to claim 1, wherein said further component comprises water present in and/or on the lipophilic polymer material.

17. A device according to claim 10, wherein said ionophore comprises valinomycin.

18. A device according to claim 10, wherein said ion forming material comprising a compound converted by the general formula as follows:

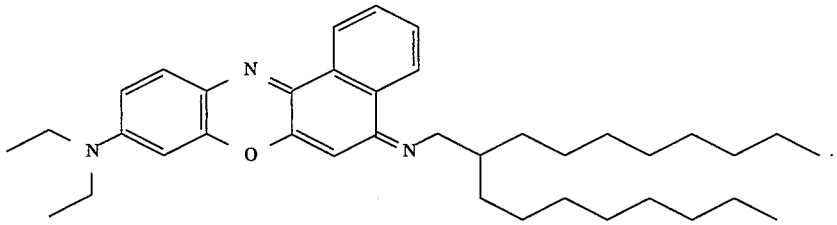

* * * * *